(12) United States Patent
Sham (10) Patent No.: US 10,293,768 B2
(45) Date of Patent: May 21, 2019

(54) AUTOMATIC IN-VEHICLE COMPONENT ADJUSTMENT

(71) Applicant: Wellen Sham, Taipei (TW)

(72) Inventor: Wellen Sham, Taipei (TW)

(73) Assignee: Wellen Sham, Taipei (TW)

( * ) Notice: Subject to any disclaimer, the term of this patent is extended or adjusted under 35 U.S.C. 154(b) by 0 days.

(21) Appl. No.: 15/675,108

(22) Filed: Aug. 11, 2017

(65) Prior Publication Data

US 2019/0047497 A1    Feb. 14, 2019

(51) Int. Cl.
| | |
|---|---|
| *B60R 16/037* | (2006.01) |
| *G01C 21/36* | (2006.01) |
| *B60Q 3/80* | (2017.01) |
| *A61B 5/00* | (2006.01) |
| *A61B 5/18* | (2006.01) |

(52) U.S. Cl.
CPC .............. *B60R 16/037* (2013.01); *A61B 5/18* (2013.01); *A61B 5/7282* (2013.01); *B60Q 3/80* (2017.02); *B60Y 2302/09* (2013.01)

(58) Field of Classification Search
None
See application file for complete search history.

(56) References Cited

U.S. PATENT DOCUMENTS

| | | | |
|---|---|---|---|
| 6,661,345 B1 | 12/2003 | Bevan et al. | |
| 7,509,212 B2 | 3/2009 | Bodin et al. | |
| 7,666,151 B2 | 2/2010 | Sullivan et al. | |
| 8,140,358 B1 | 3/2012 | Ling et al. | |
| 8,311,858 B2 | 11/2012 | Everett et al. | |
| 8,359,901 B2 | 1/2013 | Freund et al. | |
| 8,761,821 B2 | 6/2014 | Tibbitts et al. | |
| 8,787,936 B2 | 7/2014 | Tibbitts et al. | |

(Continued)

FOREIGN PATENT DOCUMENTS

| | | | | |
|---|---|---|---|---|
| DE | 102010003251 A1 | * | 9/2011 | ........... B60R 16/037 |
| DE | 10 2015 105581 A1 | | 5/2016 | |

OTHER PUBLICATIONS

Pogue, David, iPhone: The Missing Manual, Nov. 17, 2014, O'Reilly Media, 8th Edition, Chapter 2 and Chapter 4, 34 pages. Retrieved from http://techbus.safaribooksonline.com/print?xmlid=9781491947982%Fch01.

(Continued)

*Primary Examiner* — Peter D Nolan
*Assistant Examiner* — Demetra R Smith-Stewart
(74) *Attorney, Agent, or Firm* — Kilpatrick Townsend & Stockton LLP (57) ABSTRACT

Embodiments can provide a real-time system that can automatically adjust various components within a driving apparatus automatically in response to certain conditions being detected. The real-time system may be configured to control these components in response to detection of certain conditions, which may include external conditions and/or internal conditions. In some embodiments, a user of the driving apparatus may be facilitated to provide his/her personal settings to configure the real-time system. In those embodiments, an interface may be provided to the user to instruct the real-time system to adjust one or more components within the driving apparatus in accordance with the user provided personal settings in response to one or more specific conditions being detected.

18 Claims, 4 Drawing Sheets

(56) References Cited

U.S. PATENT DOCUMENTS

| | | | |
|---|---|---|---|
| 8,892,451 B2 | 11/2014 | Everett et al. | |
| 8,924,240 B2 | 12/2014 | Depura et al. | |
| 9,053,516 B2 | 6/2015 | Stempora | |
| 9,094,816 B2 | 7/2015 | Maier et al. | |
| 9,141,975 B2 | 9/2015 | Meller | |
| 9,162,753 B1 | 10/2015 | Panto et al. | |
| 9,440,657 B1 | 9/2016 | Fields et al. | |
| 9,460,601 B2 * | 10/2016 | Mimar | G08B 21/0476 |
| 9,694,771 B1 | 7/2017 | Ding | |
| 9,809,169 B1 * | 11/2017 | Naboulsi | B60R 1/025 |
| 2003/0204290 A1 | 10/2003 | Sadler et al. | |
| 2006/0167597 A1 | 7/2006 | Bodin et al. | |
| 2006/0212195 A1 | 9/2006 | Veith et al. | |
| 2008/0074307 A1 | 3/2008 | Boric-Lubecke et al. | |
| 2008/0163670 A1 | 7/2008 | Georgeson | |
| 2008/0191863 A1 | 8/2008 | Boling et al. | |
| 2009/0293589 A1 | 12/2009 | Freund et al. | |
| 2010/0134627 A1 | 6/2010 | Yen et al. | |
| 2010/0222976 A1 | 9/2010 | Haug | |
| 2011/0090047 A1 | 4/2011 | Patel | |
| 2011/0307123 A1 | 12/2011 | Abe et al. | |
| 2012/0303392 A1 | 11/2012 | Depura et al. | |
| 2013/0027208 A1 | 1/2013 | Tao | |
| 2013/0070043 A1 | 3/2013 | Geva et al. | |
| 2013/0204153 A1 | 8/2013 | Buzhardt | |
| 2013/0297099 A1 | 11/2013 | Rovik | |
| 2014/0039934 A1 | 2/2014 | Rivera | |
| 2014/0089101 A1 | 3/2014 | Meller | |
| 2014/0293053 A1 | 10/2014 | Chuang | |
| 2014/0309564 A1 * | 10/2014 | Jensen | A61H 31/006 601/41 |
| 2014/0309864 A1 * | 10/2014 | Ricci | H04W 48/04 701/36 |
| 2015/0019266 A1 | 1/2015 | Stempora | |
| 2015/0025917 A1 | 1/2015 | Stempora | |
| 2015/0127215 A1 * | 5/2015 | Chatterjee | H04W 4/001 701/36 |
| 2015/0140954 A1 | 5/2015 | Maier et al. | |
| 2015/0160019 A1 * | 6/2015 | Biswal | G01C 21/26 701/1 |
| 2015/0197205 A1 | 7/2015 | Xiong et al. | |
| 2015/0263886 A1 | 9/2015 | Wang et al. | |
| 2015/0328985 A1 | 11/2015 | Kim et al. | |
| 2015/0334545 A1 | 11/2015 | Maier et al. | |
| 2016/0001781 A1 | 1/2016 | Fung et al. | |
| 2016/0042637 A1 | 2/2016 | Cahill | |
| 2016/0180144 A1 | 6/2016 | Tatourian et al. | |
| 2016/0272200 A1 * | 9/2016 | Prokhorov | G05D 1/0293 |
| 2016/0272214 A1 | 9/2016 | Sham | |
| 2016/0330601 A1 | 11/2016 | Srivastava | |
| 2017/0011562 A1 | 1/2017 | Hodges | |
| 2017/0067747 A1 * | 3/2017 | Ricci | H04W 4/21 |
| 2017/0174158 A1 | 6/2017 | Ding | |
| 2017/0247000 A1 * | 8/2017 | Ricci | G06K 9/00302 |
| 2017/0270490 A1 * | 9/2017 | Penilla | G06Q 10/1095 |
| 2017/0305349 A1 * | 10/2017 | Naboulsi | B60R 1/04 |
| 2017/0355377 A1 | 12/2017 | Vijaya Kumar et al. | |
| 2018/0000397 A1 | 1/2018 | Sham | |

OTHER PUBLICATIONS

U.S. Appl. No. 14/977,627, filed Dec. 21, Non-Final Rejection dated Apr. 7, 2016, all pages.

U.S. Appl. No. 14/977,627, filed Dec. 21, 2015 Final Rejection dated Oct. 20, 2016, all pages.

U.S. Appl. No. 14/977,627, filed Dec. 21, 2015 Notice of Allowance dated Feb. 28, 2017, all pages.

U.S. Appl. No. 15/199,268, filed Jun. 30, 2016 Non-Final Rejection dated Nov. 9, 2016, all pages.

U.S. Appl. No. 15/199,268, filed Jun. 30, 2016 Final Rejection dated Jun. 8, 2017, all pages.

U.S. Appl. No. 15/199,268, filed Jun. 30, 2016 Non-Final Rejection dated Feb. 20, 2018, all pages.

Droitcour et al, "Signal-to-Noise Ratio in Doppler Radar System for Heart and Respiratory Rate Measurements." IEEE Transactions on Microwave Theory and Techniques, vol. 57, No. 10, Oct. 2009, 10 pages.

Lu et al., "A New Stochastic Model to Interpret Heart Rate Variability." Proceedings on the 25th Annual International Conference of the IEEE EMBS. Sep. 17-21, 2003.

European Search Report for EP17179153 dated Oct. 19, 2017, all pages.

U.S. Appl. No. 15/675,142, filed Aug. 11, 2017 Non-Final Rejection dated Dec. 6, 2017, all pages.

* cited by examiner

AUTOMATIC IN-VEHICLE COMPONENT ADJUSTMENT

CROSS-REFERENCES TO RELATED APPLICATIONS

The present disclosure relates to the following applications: U.S. Nonprovisional application Ser. No. 15/199,268, filed Jun. 30, 2016; U.S. Nonprovisional application Ser. No. 14/977,627, filed Dec. 21, 2015; and U.S. Nonprovisional application Ser. No. 15/063,435, filed Mar. 7, 2016. The entire contents of each of these applications are incorporated by reference herein for all purposes.

BACKGROUND OF THE INVENTION

The present disclosure relates to controlling settings of one or more components within a driving an apparatus.

Traditionally, settings of various vehicle components can be configured or adjusted by a user of the vehicle prior to operating the vehicle. For example, a seat in the vehicle may be adjusted or configured by the user prior to operating the vehicle. During the operation of the vehicle, while some components may be adjusted, some other components may not be adjusted. For example, components such as air conditioning system, passenger side seat, or entertainment system, window system are typically adjustable during the operation of the vehicle. However, settings of certain components such as driver's seat and certain driving features may not be adjusted during the operation of the vehicle.

Certain conditions can occur during the operation of vehicle unexpectedly. For example, a weather condition such as heavy rain storm or snow storm can happen during the operation of the vehicle. Typically, when such a weather condition takes place unexpectedly, a user of the vehicle, either driver or passenger, may need to manually adjust the windshield wiper, and/or adjust the A/C system to demositurize or de-frost the windshield.

While these manual adjustments of vehicle components may be relatively easy to be implemented by the driver of the vehicle in response to the weather condition, other adjustments in response to other conditions may not be so easy to be implemented. For example, a fatigue condition can occur for the driver of the vehicle, and certain adjustments of vehicle settings may be desired as a response. For instance, the speed of vehicle may need to be reduced, a self-driving feature may need to be activated, or an audible alert may need to be generated to alert the driver. However, manual adjustments of such vehicle settings to address the fatigue condition of the driver may not be feasible when the driver is fatigued or sleepy.

Accordingly, there is a need to have a driving apparatus to automatically adjust certain settings of one or more vehicle components when one or more conditions are detected.

BRIEF SUMMARY OF THE INVENTION

Embodiments can provide a real-time system configured to automatically adjust settings of one or more components within a driving apparatus in response to detection of one or more conditions while a driving apparatus is moving. As used herein, two types of conditions may be relevant for adjusting the settings of the components. One type of conditions may be referred to as external conditions. Those conditions may include weather conditions, road conditions, traffic conditions, local conditions, and/or any other external conditions. The other type of conditions may be referred to as internal conditions or personal conditions. Those conditions may include fatigue conditions of an operator of the driving apparatus (e.g., the operator is drowsy or sleepy), health hazard or medical conditions of an user of the driving apparatus (e.g., an operator or a passenger suffers a seizure or a heart attack), ambient conditions within a cabin of the driving apparatus (e.g., a temperature, humidity level within the cabin), mechanical and/or electrical conditions of the driving apparatus, and/or any other internal conditions.

The real-time system in accordance with the disclosure can be configured to adjust settings of one or more components within the driving apparatus in response to occurrence of one or more of the external conditions and/or internal conditions having been detected. For example, as illustration, the real-time system can automatically play a song through the entertainment system of the driving apparatus at a preset high volume to alert the operator when a fatigue condition is detected for the operator. As another example, the real-time system can be configured to open the sun-roof when the ambient weather condition is detected to be within a pleasant temperature range.

In some embodiments, more than one components within the driving apparatus may be adjusted when a certain condition is detected. For example, still as illustration, when the fatigue condition is detected for the operator of the driving apparatus, the real-time system may vibrate the operator's seat for a number of seconds and start playing a song at the preset high volume for its entirety. If the fatigue condition is still being detected for the operator, the real-system may activate the self-driving feature and take the operation of the driving apparatus from the operator. In some embodiments, the real-system may also start a telecommunication system to notify a relevant authority that the operator may be suffering a debilitating condition to prevent the operator from continuing to operate the driving apparatus.

In some embodiments, a user of the driving apparatus may be facilitated to set a preference as to which components and what settings to be adjust in response to a specific condition has been detected for the user. For example, as illustration, the operator of the driving apparatus can provide a personal setting to instruct the real-time system to start playing a song of the operator's choice at a volume selected by the operator. The operator may specify, through the personal settings, that the real-time system may not vibrate the seat when the fatigue condition is detected for the operator.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION OF THE INVENTION

Controlling a component within a driving apparatus is generally known in the art. Many existing technologies typically require human intervention to adjust the component within the driving apparatus. While certain components within the driving apparatus may be automatically adjusted, such as the brightness of the passenger lamp, automatic adjustment of these components typically does not respond to detections of one or more conditions. It is generally known that a headlight of a vehicle may be automatically turned on when it becomes dark.

In accordance with the disclosure, embodiments can provide a real-time system that can automatically adjust one or more components within a driving apparatus automatically in response to one or more conditions being detected. The one or more components that can be automatically controlled by the real-time system may include an audio module, air conditioning module, seat control module, interior lighting module, window control module, sunroof control module, mirror control module, telematics control module, and/or any other components within the driving apparatus. The real-time system may be configured to control one or more of these components in response to detection of one or more certain conditions, which may include external conditions and/or internal conditions. The external conditions may be referred to those conditions external to the driving apparatus, such as weather conditions, road conditions, traffic conditions, local conditions and/or any other conditions external to the driving apparatus. The internal conditions may be referred to those conditions internal to driving apparatus, such as fatigue conditions of an operator of the driving apparatus, medical conditions of a user of the driving apparatus, ambient conditions within a cabin of the driving apparatus, mechanical and/or electrical conditions to one or more parts of the driving apparatus, and/or any other internal conditions.

In some embodiments, a user of the driving apparatus may be facilitated to provide his/her personal settings to configure the real-time system. In those embodiments, an interface may be provided to the user to instruct the real-time system to adjust one or more components within the driving apparatus in accordance with the user provided personal settings in response to one or more specific conditions being detected.

Various specific embodiments of the present disclosure will be described below with reference to the accompanying drawings constituting a part of this specification. It should be understood that, although structural parts and components of various examples of the present disclosure are described by using terms expressing directions, e.g., "front", "back", "upper", "lower", "left", "right" and the like in the present disclosure, these terms are merely used for the purpose of convenient description and are determined on the basis of exemplary directions displayed in the accompanying drawings. Since the embodiments disclosed by the present disclosure may be set according to different directions, these terms expressing directions are merely used for describing rather than limiting. Under possible conditions, identical or similar reference numbers used in the present disclosure indicate identical components.

Figure 1:
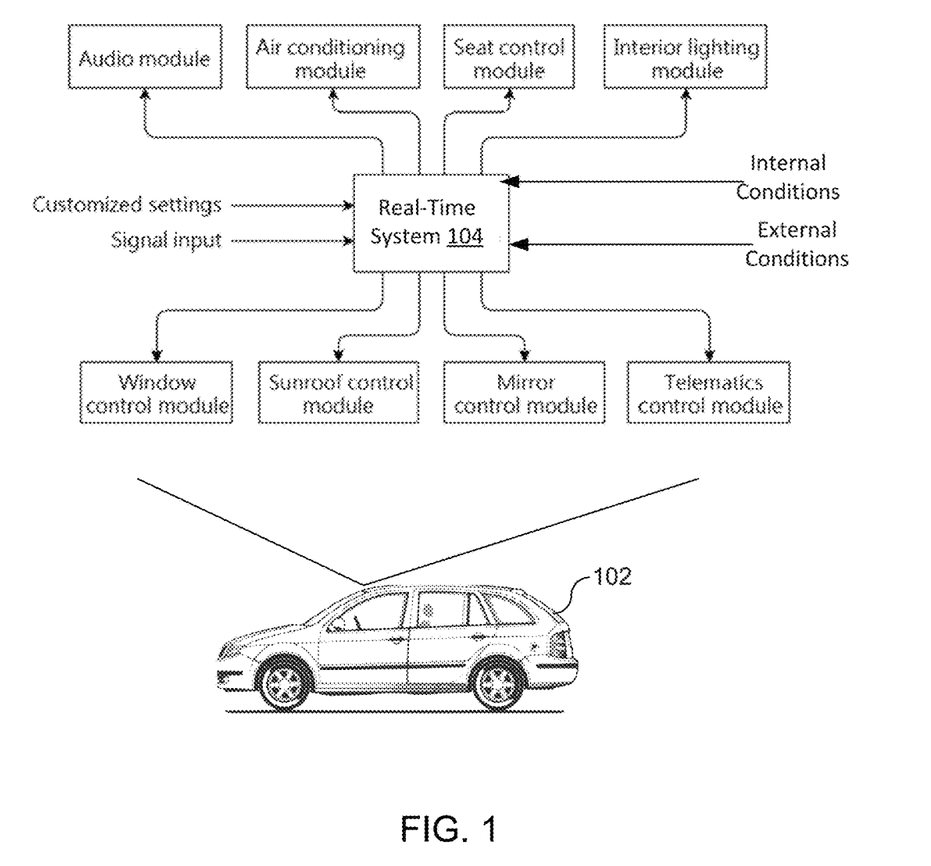
FIG. 1 generally illustrates an infrastructure for automatically adjusting one or more components in response to one or more conditions being detect in accordance with the disclosure.

FIG. 1 generally illustrates an infrastructure for automatically adjusting one or more components in response to one or more conditions being detect in accordance with the disclosure. As show, a real-time system 104 configured to automatically adjust one or more components within the driving apparatus 102 may be provided within the driving apparatus 102. The driving apparatus 102 may include any driving apparatus that moves in distance. Examples of driving apparatus 102 may include a vehicle such as a car, a bus, a train, a truck, a tram, or any other type of vehicle; may include a vessel such as a boat, a ship, a barge, a ferry or any other type of watercraft; may include an aircraft such as an airplane, a spaceship, or any other type of aircraft; or may include any other transportation apparatus. In one example, the driving apparatus 102 is an electrical automobile. As shown, the driving apparatus 102 can generate or receive condition information from time to time. The condition information can include information indicating occurrence of one or more external conditions having been detected, information indicating occurrence of one or more internal conditions have been detected, and/or any other information.

As described herein, the external condition information may include weather conditions, road conditions, traffic conditions, local conditions, and/or any other external conditions. The external condition information may be received by driving apparatus 102 wirelessly, for example via satellite, radio, GPS, and/or any other wireless communication means. For example, as illustrations, the driving apparatus 102 may receive weather condition information via a satellite service, a radio service, and/or any other means. For instance, weather conditions may be broadcast in certain areas via radio frequencies and may be received by the driving apparatus 102. As another example, traffic conditions in the areas where the driving apparatus 102 is traveling in may be received by the driving apparatus 102 via a GPS service. Still as another example, road conditions indicating curvatures, bumps, slope, number of lanes and/or any other road conditions may be received via a map service or a GPS service. The local conditions may include conditions regarding local events (e.g., a local event with more than 1000 attendees is being held) or local attractions (e.g., a beach is located 2 miles ahead) in the areas where the driving apparatus is traveling in. Such local conditions may be received by the driving apparatus 102 via radio, a subscribed a local information service, a map service, a GPS service, and/or any other type of channels.

As described herein, the internal condition information may include information indicating detection of occurrence of a fatigue condition of an operator of the driving apparatus 102, a health hazard or medical condition of a user (e.g., an operator or a passenger) of the driving apparatus 102, an ambient condition within a cabin of driving apparatus 102, mechanical or electrical conditions of the driving apparatus 102. Such internal information can be generated by the driving apparatus 102 in some embodiments. For example, U.S. application Ser. No. 15/675,142 entitled "IN VEHICLE FATIGUE MONITORING SYSTEM," filed concurrently herewith, describes detecting a fatigue condition for the operator of the driving apparatus, which is incorporated herein by reference in its entirety. As another example, U.S. application Ser. No. 15/199,268, entitled "HEART RELATED INDIVIDUAL FINGERPRINT," filed Jun. 30, 2016 describes detecting a medical condition of a person within the driving apparatus, which is also incorporated herein by reference in its entirety. Detection of those internal conditions will not be described in details herein, and please refer to the above-mentioned applications for such details.

In some embodiments, the driving apparatus 102 may be equipped with one or more sensors for detecting ambient conditions within a cabin of the driving apparatus 102. For example, the driving apparatus 102 may be equipped with a temperature sensor configured to detect a temperature and/or humidity condition within the driving apparatus 102. As another example, the driving apparatus 102 may be equipped with a smoke detector configured to detect a smoke condition within the driving apparatus 102. Still as another example, the driving apparatus 102 may be equipped with a noise detector configured to detect a noise condition within the driving apparatus 102.

In some embodiments, the driving apparatus 102 may be equipped with one or more sensors or diagnostic devices for detecting a mechanical condition or an electrical condition of one or more parts of the driving apparatus 102. For example, a level of battery level may be determined by the driving apparatus 102. As another example, occurrence of certain mechanical failures, such as brake system, steering system, throttle system of the driving apparatus 102 can be detected by the driving apparatus 102.

As shown, the real-time system 104 may be configured to receive the internal and/or external condition information. The real-time system 104 may be configured to automatically adjust certain components within the driving apparatus 102 in response to occurrence of one or more conditions having been detected as indicated by the received internal and/or external condition information. For example, as illustration, the real-time system 104 may be configured to automatically start playing a particular song at a preset high volume when a fatigue condition is detected for the operator of the driving apparatus 102. As another example, the real-time system 104 may be configured to close an open window of the driving apparatus 102 when a rain condition is detected in an area where the driving apparatus 102 is travelling in.

As also shown, the real-time system 104 can be configured to receive from a user of the driving apparatus 102 personal settings for automatically adjusting one or more components within driving apparatus 102 in response to one or more conditions specified by the user. For example, an interface may be provided to the operator of the driving apparatus 102 to enable the operator to specify which component or components to be adjusted and how to adjust those components in response to detection of a fatigue condition of the operator. For example, the operator may be enabled to instruct the real-time system 104 to play a specific song of the operator's choice at a volume of the operator's choice when the fatigue condition is detected for the operator. As another example, the operator may be enabled to instruct the real-time system 104 to vibrate the operator's seat for a number of seconds specified by the operator when the fatigue condition is detected for the operator.

That is, in some embodiments, the operator of the driving apparatus 102 may be enabled to specify one or more rules for automatically adjusting one or more components within the driving apparatus 102 in response to one or more conditions having been detected. In some embodiments, the rules specified by the operator of driving apparatus 102 may create a configuration for the one or more components. In some embodiments, the rules specified by the operator of the driving apparatus 102 may override the default rules originally configured into real-time system 104.

For example, as an illustration, the operator of driving apparatus 102 may provide personal settings for controlling the A/C system such as temperature, wind direction, wind strength, moisture level, and/or any other A/C aspects in response to a whether condition having been detected. In that example, the operator of driving apparatus 102 may also provide personal settings for controlling the window system when the weather condition is detected. For instance, the operator of the driving apparatus may specify that when the temperature in the area where the driving apparatus 102 is traveling in is above 90 degrees, the real-system 104 should control the A/C system to ensure the temperature setting is between 72-78 degrees, wind directions is at least towards the operator, and wind strength should be at full. If one or more of these settings are not met, the real-time system 104 should adjust them to those settings. The operator may also specify when such a weather condition is detected, the real-system 104 should ensure sun-roof is closed and all side windows are closed, and if any of those windows are open, the real-time system 104 should automatically close the window.

As another example, the real-time system 104 may be initially configured to play a random song at a preset volume when a fatigue condition is detected for the operator as an alert to the operator. Through the interface, the operator can be enabled to modify this configuration. For instance, the operator may specify a particular song of the operator's choice and a volume of the operator's choice for playing the song. The operator may also specify that the real-time system 104 should vibrate the operator's seat for 10 seconds when the fatigue condition is detected, in addition to playing the song.

In some embodiment, the interface described herein for enabling a user of the driving apparatus 102 to provide personal settings to the real-time 104 may be provided within the driving apparatus 102. For example, such an interface may be called up on a touch screen arranged on a dashboard of the driving apparatus 102. However, this is not necessarily the only case. In some embodiments, the interface may be provided remotely on a smartphone of the user or a computer of the user. For example, the user may be enabled to provide the personal settings through an app on his/her smart phone. The personal setting data provided by the user through the app can be transmitted to driving apparatus 102 wirelessly via a server to configure the real-time system 104.

Figure 2:
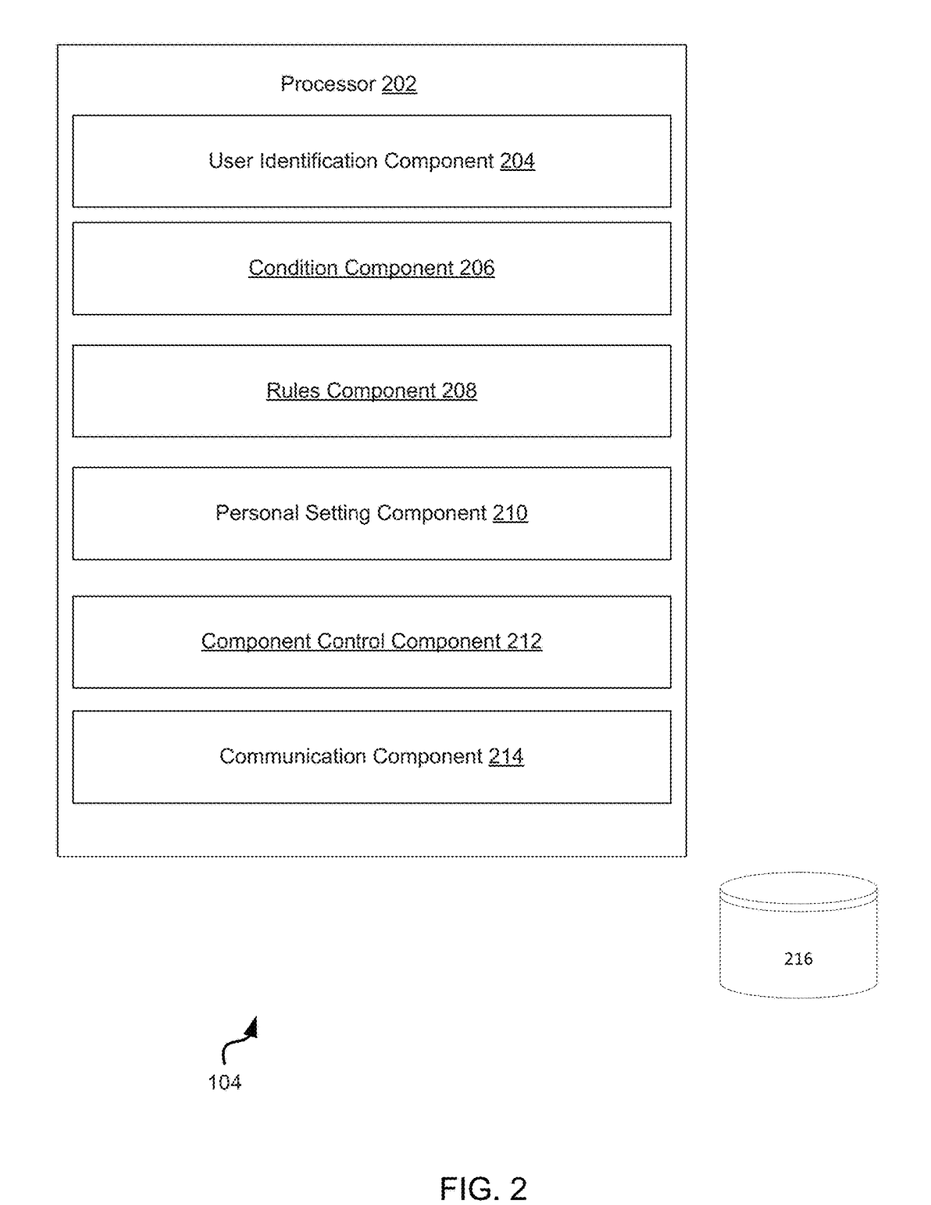
FIG. 2 illustrates an exemplary structure of the real-time system shown in FIG. 1 in accordance with the disclosure.

With the infrastructure for automatically adjusting one or more components within a driving apparatus having been generally described, attention is now directed to FIG. 2. FIG. 2 illustrates an exemplary structure of the real-time system 104 shown in FIG. 1 in accordance with the disclosure. As shown, the real-time system 104 can include one or more of a processor 202 configured to implement computer program components, a storage device 216 and/or any other components. The computer program components can include a user identification component 204, a condition component 206, a rules component 208, a personal setting component 210, a component controlling component 212, a communication component 214 and/or any other components. In some embodiments, the real-time system 104 may be arranged within the driving apparatus 102. In those embodiments, the real-time system 104 may be configured to communicate with various sensors and devices for the condition information described herein through short range communication methods, such as Bluetooth, WiFi and/or any short range communication methods. In some embodiments, the real-time system 104 may be arranged within a control center, for example as a remote server provided by the control center. In those embodiments, the real-time system 104 may be configured to communicate with the various sensors and devices through a communications network.

The user identification component 204 can be configured to identify the operator of the driving apparatus 102. The identification of the operator by the user identification component 204 can be made based on the fingerprint image acquired by a fingerprint detection component provided in the driving apparatus 102, the image of operator's face captured by an image capturing device arranged within the driving apparatus 102, and/or any other identification information regarding operator. For example, the identification by the user identification component 204 may involve analyzing features in the fingerprint image and/or in the facial image of the operator, and compared the obtained features with features of registered operators. Upon a match, the user identification component 204 can be configured to obtain a user ID of the identified operator.

The condition component 206 can be configured to receive condition information indicating occurrence of one or more conditions has been detected. The condition information received by the condition component 206 can include internal condition information, external condition information as described herein, and/or any other information. In some embodiments, the condition component 206 may be configured to generate different control signals to indicate occurrence of different conditions has been detected as indicated by the received condition information.

The rules component 208 may be configured to retrieve one or more rules specifying setting adjustment for a certain component within the driving apparatus 102 in response to one or more conditions having been detected as indicated by the condition component condition component 206. An individual rule retrieved by the rules component 208 may specify a specific component to be adjusted, such as one of the components shown in FIG. 1, a target setting for adjusting the specific component, a triggering condition matching one of the condition(s) detected), and/or any other information.

For example, as illustration, the rules retrieved by the rules component 208 may include a rule specifying an entertainment system should be activated to play a specific song when a fatigue condition is detected for the operator. As another example, the rules may include a rule specifying a self-driving feature should be activated when a heart condition is detected for the operator. Still as another example, the rules may include a rule specifying a sun-roof of the driving apparatus 102 may be slid open when a weather condition of sunny sky with temperature above 70 degree is detected. Yet as an example, the rules may include a rule specifying when a debilitating condition (such as seizure) is detected for the operator of the driving apparatus 102, the telecommunication system should be activated to notify a relevant agency (such as a control center) of the operator's debilitating condition, the self-driving features should be activated to take the operation control over from the operator, and emergency lights of the driving apparatus 102 may be flashed to warn surrounding entities (e.g., person, other vehicle, etc.) to avoid the driving apparatus. As another example, the rules may include a rule specifying an A/C system may be activated to demositurize the windshield when a weather condition of rain storm is detected and also specifying the window system should be instructed to close all windows of the driving apparatus 102.

The personal setting component 210 can be configured to receive personal setting data from a user of the driving apparatus 102. In some examples, the personal setting component 210 can be configured to create one or more new rules for adjusting the components within the driving apparatus 102. In some embodiments, the personal setting component 210 can be configured to specify additional settings for adjusting the components according to the existing rules using the personal setting data provided by the user. In some embodiments, the personal setting component 210 can be configured to override one or more existing rules with the received personal setting data.

The component controlling component 212 can be configured to control one or more components within the driving apparatus 102 in accordance with the rules retrieved by the rules component 208 and/or in accordance with the personal setting data received by the personal setting component 210. In implementations, the component controlling component 212 can be configured to receive control signals from the condition component 206, which may indicate one or more conditions have been detected. In response to receiving such control signals from the condition component 206, the component controlling component 212 can be configured to instruct the rules component 206 to retrieve rules and find one or more rules matching the one or more conditions that have been detected.

In some embodiments, the component controlling component 212 can be configured to effectuate adjustment of one or more components within the driving apparatus 102 in accordance with the one or more rules matching the condition(s) detected. In implementations, for achieving this, the component controlling component 212 can be configured to generate specific control commands to adjust the components according to the rules matching the conditions detected. For example, the component controlling component 212 can generate a specific control command to instruct the A/C system to increase lower the temperature setting to 70 degree when an ambient condition of 80 degree within a cabin of the driving apparatus 102 is detected.

In some embodiments, the component controlling component 212 may be configured to generate control commands to effectuate adjustment of multiple components within the driving apparatus 102 simultaneously or substantially simultaneously. For example, in response to a rule specifying three different components (e.g., A/C, sun-roof, and window) should be adjusted specifically according to the rule, the component controlling component 212 may generate three different control commands to effectuate the adjustment of the three components according to the rule simultaneously or substantially simultaneously.

The communication component 314 can be configured to communicate the condition information received by condition component 206, the identification information regarding the operator 202 as identified by the user identification component 204, the component adjustment made by the component controlling component 212, and/or any other information to a control center, and/or any other entities. The communication component 314 can be configured to communicating such information via a communications network.

The storage device 216 may be configured to store and provide the rules and/or personal setting data described herein. In implementations, the storage device 216 may include a memory storage device, a disk storage device, a cloud storage device, and/or any other type of storage device.

It should be understood the above-described functionalities attributed to real-time system 104 can be implemented within the driving apparatus 102. However, this is not necessarily the only case. In certain embodiment, part of or the entire functionalities attributed to real-time system 104 herein can be implemented at the control center. For example, the control center may comprise a server that can be configured to perform part of the operations provided by real-time system 104 as described above.

Figure 3:
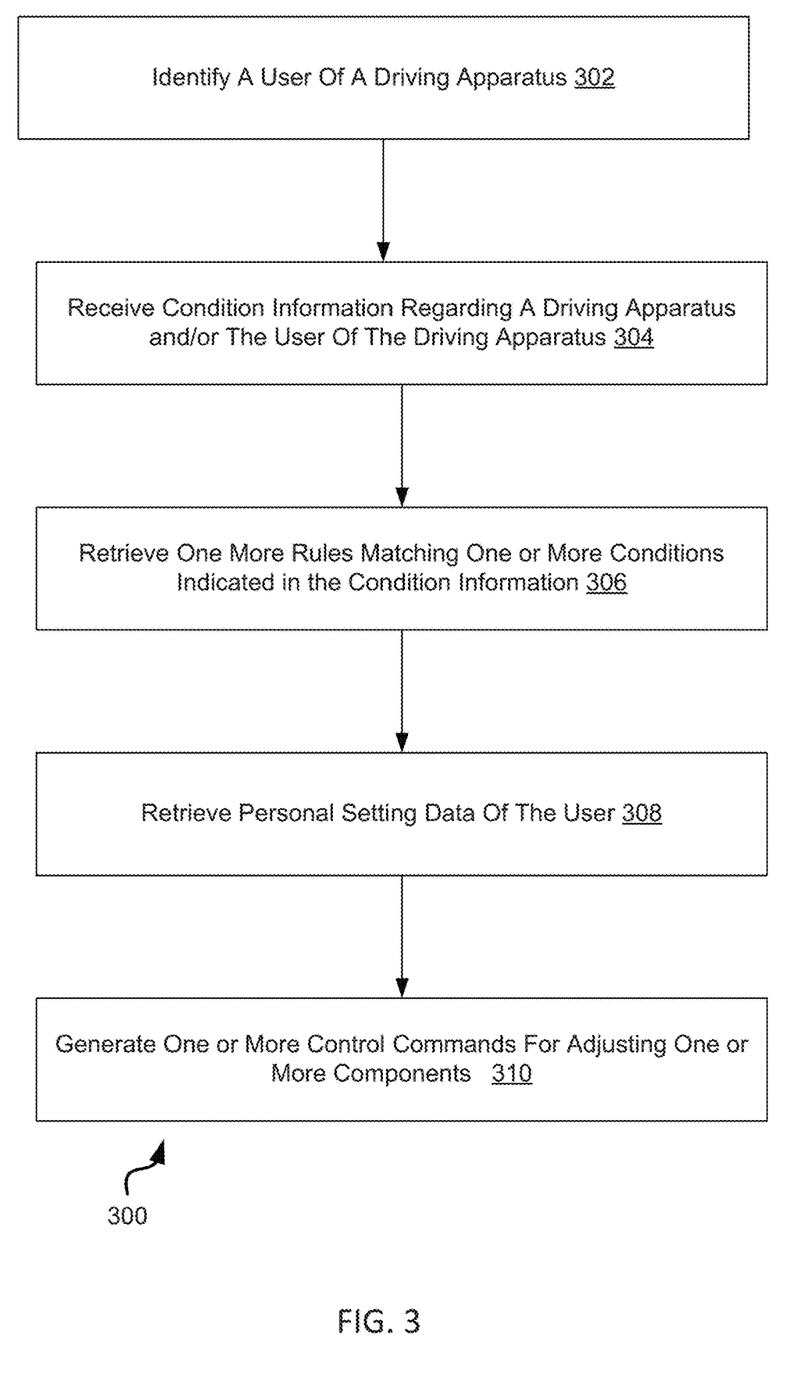
FIG. 3 illustrates one exemplary method for automatically adjusting one or more components within a driving appa

FIG. 3 illustrates one exemplary method for automatically adjusting one or more components within a driving apparatus in response to one or more conditions having detected in accordance with the disclosure. The operations of method 300 presented below are intended to be illustrative. In some embodiments, method 300 may be accomplished with one or more additional operations not described and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At 302, a user of the driving apparatus can be identified. In some implementations, operation 302 can be performed by a user identification component substantially similar to or the same as the user identification component 204 as described and illustrated herein.

At 304, condition information regarding the driving apparatus and/or the user identified at 302 can be received. The condition information can include internal condition information described herein, external condition information described herein, and/or any other type of information. The condition information received at 304 can indicate occurrence of one or more conditions has been detected for the driving apparatus and/or the user. In some implementations, operation 304 can be performed by a condition component the same as or substantially similar to condition component 206 described and illustrated herein.

At 306, In some implementations, in response to the detection of the occurrence of the one or more conditions as indicated by the condition information received at 304, one or more rules can be retrieved. A given one of the one or more rules retrieved at 306 may specify at least one component within the driving apparatus 102 to be adjusted, at least one target setting for adjusting the at least one component, at least one triggering condition that triggers the adjustment of the at least one component as specified in the given rule. The one or more rules may be retrieved at 306 by virtue of the triggering conditions specified in the one or more rules matching the one or more conditions indicated by the condition information received at 304. In some implementations, operations involved in 308 can be performed by a rules component the same as or substantially similar to rules component 208 described and illustrated herein.

At 308, personal setting data may be retrieved for the user identified at 302. In some examples, the personal setting data may specify one or more target settings in addition to those specified in the one or more rules retrieved at 306. In some examples, the personal setting data retrieved at 308 may override some or all of the one or more rules retrieved at 306. In some implementations, operation 308 can be performed by personal setting component the same as or substantially similar to personal setting component 210 described and illustrated herein.

At 310, one or more control commands can be generated to adjust the settings of the one or more components in accordance with the rules retrieved at 306 and/or the personal setting data retrieved at 308. In some implementations, operation 310 can be performed by component controlling component the same as or substantially similar to component controlling component 212 described and illustrated herein.

Figure 4:
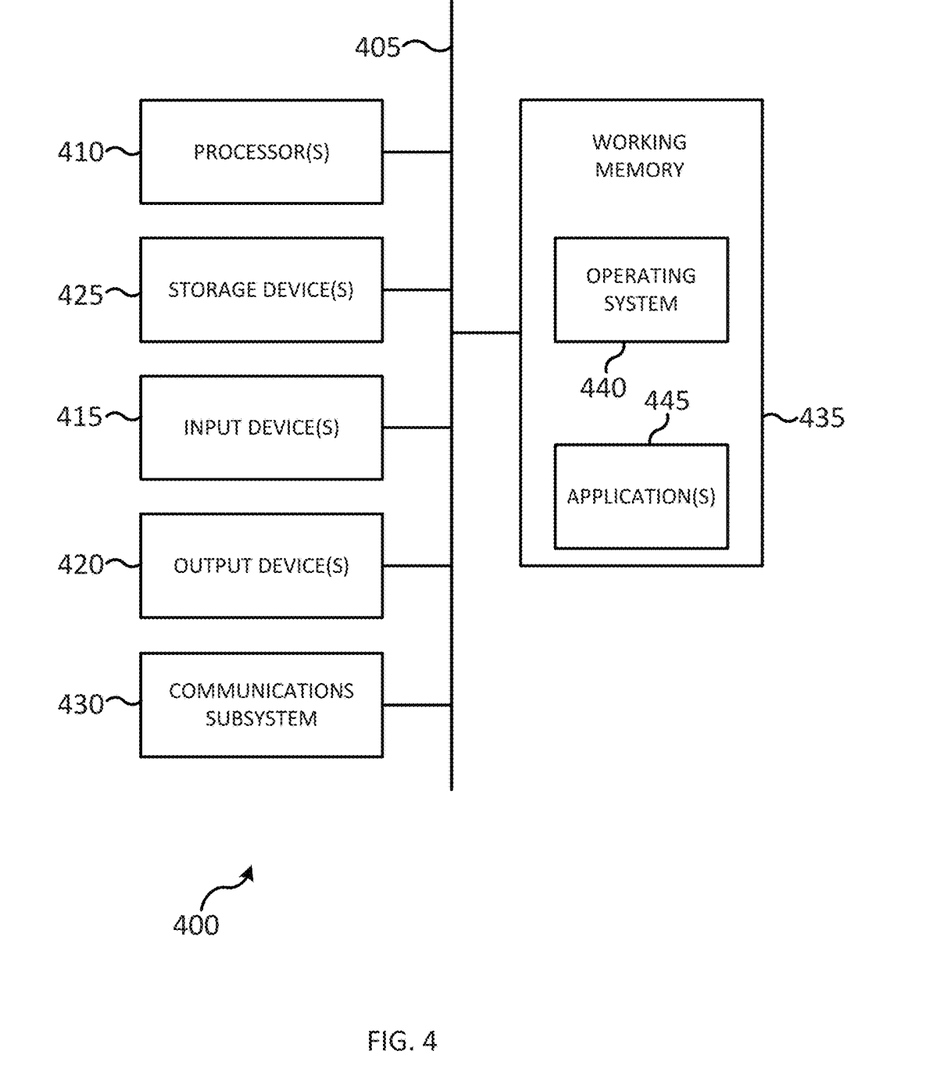
- FIG. 4 illustrates a simplified computer system, according to an exemplary embodiment of the present disclosure

FIG. 4 illustrates a simplified computer system, according to an exemplary embodiment of the present disclosure. A computer system 400 as illustrated in FIG. 4 may be incorporated into devices such as a portable electronic device, mobile phone, or other device as described herein. FIG. 4 provides a schematic illustration of one embodiment of a computer system 400 that can perform some or all of the steps of the methods provided by various embodiments. It should be noted that FIG. 4 is meant only to provide a generalized illustration of various components, any or all of which may be utilized as appropriate. FIG. 4, therefore, broadly illustrates how individual system elements may be implemented in a relatively separated or relatively more integrated manner.

The computer system 400 is shown comprising hardware elements that can be electrically coupled via a bus 405, or may otherwise be in communication, as appropriate. The hardware elements may include one or more processors 410, including without limitation one or more general-purpose processors and/or one or more special-purpose processors such as digital signal processing chips, graphics acceleration processors, and/or the like; one or more input devices 415, which can include without limitation a mouse, a keyboard, a camera, and/or the like; and one or more output devices 420, which can include without limitation a display device, a printer, and/or the like.

The computer system 400 may further include and/or be in communication with one or more non-transitory storage devices 425, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 400 might also include a communications subsystem 430, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 430 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 430. In other embodiments, a portable electronic device, e.g. the first electronic device, may be incorporated into the computer system 400, e.g., an electronic device as an input device 415. In some embodiments, the computer system 400 will further comprise a working memory 435, which can include a RAM or ROM device, as described above.

The computer system 400 also can include software elements, shown as being currently located within the working memory 435, including an operating system 440, device drivers, executable libraries, and/or other code, such as one or more application programs 445, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 4, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 425 described above. In some cases, the storage medium might be incorporated within a computer system, such as computer system 400. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 400 and/or might take the form of source and/or installable code, which, upon compilation and/or installation on the computer system 400 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 400 to perform methods in accordance with various embodiments of the technology. According to a set of embodiments, some or all of the procedures of such methods are performed by the computer system 400 in response to processor 410 executing one or more sequences of one or more instructions, which might be incorporated into the operating system 440 and/or other code, such as an application program 445, contained in the working memory 435. Such instructions may be read into the working memory 435 from another computer-readable medium, such as one or more of the storage device(s) 425. Merely by way of example, execution of the sequences of instructions contained in the working memory 435 might cause the processor(s) 410 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 400, various computer-readable media might be involved in providing instructions/code to processor(s) 410 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 425. Volatile media include, without limitation, dynamic memory, such as the working memory 435.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 410 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 400.

The communications subsystem 430 and/or components thereof generally will receive signals, and the bus 405 then might carry the signals and/or the data, instructions, etc. carried by the signals to the working memory 435, from which the processor(s) 410 retrieves and executes the instructions. The instructions received by the working memory 435 may optionally be stored on a non-transitory storage device 425 either before or after execution by the processor(s) 410.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram.

Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method for automatically adjusting one or more component settings of a driving apparatus, the method being implemented in a processor configured to execute machine-readable instructions, the method comprising:
   identifying a user of the driving apparatus;
   receiving condition information regarding an external condition about the driving apparatus, wherein the condition information indicates occurrence of the external condition has been detected;
   in response to the detection of the occurrence of the external condition as indicated by the condition information, retrieving one or more rules matching the external condition, wherein a given one of the one or more rules specifies a component within the driving apparatus to be adjusted, a specific target setting for the adjustment, and a condition that triggers the adjustment of the component;
   based on the one or more rules, determine one or more components for adjustment by virtue occurrence of the external condition;
   retrieving personal setting data for the identified user, the retrieved personal setting data including one or more target settings for adjusting the component as specified in the given rule; and
   generating one or more control commands for adjusting settings of the one or more components based on the retrieved rules and personal setting data.

2. The method of claim 1, wherein the external condition includes one of a weather condition, a road condition, and a traffic condition in an area where is driving apparatus is traveling in.

3. The method of claim 1, wherein the condition information includes at least one of a fatigue condition and a medical condition regarding the user.

4. The method of claim 1, wherein the condition information includes at least one of an ambient condition within a cabin of the driving apparatus, a mechanical condition of the driving apparatus, and an electrical condition of the driving apparatus.

5. The method of claim 1, wherein the personal setting data overrides the target setting specified in the given rule.

6. The method of claim 1, wherein the personal setting data specify at least one additional target setting for adjusting the component specified in the given rule.

7. The method of claim 1, wherein the component specified in the given rule includes at least one of: an audio module, air conditioning module, seat control module, interior lighting module, window control module, sunroof control module, mirror control module, and telecommunication module of the driving apparatus.

8. The method of claim 1, wherein the driving apparatus includes a vehicle, a train, a ship, or an airplane.

9. The method of claim 1, further comprising: receiving the personal setting data from the user via an interface, the interface being presented to user on a portable computing device associated with the user.

10. A system for automatically adjusting one or more component settings of a driving apparatus, the system comprising one or more processors configured to execute machine-readable instructions, wherein when the machine-readable instructions are executed, the one or more processors are caused to perform:
    identifying a user of the driving apparatus;
    receiving condition information regarding an external condition about the driving apparatus, wherein the condition information indicates occurrence of the external condition has been detected;
    in response to the detection of the occurrence of the external condition as indicated by the condition information, retrieving one or more rules matching the external condition, wherein a given one of the one or more rules specifies a component within the driving apparatus to be adjusted, a specific target setting for the adjustment, and a condition that triggers the adjustment of the component;
    based on the one or more rules, determining one or more components for adjustment by virtue occurrence of the external condition;
    retrieving personal setting data for the identified user, the retrieved personal setting data including one or more target settings for adjusting the component as specified in the given rule; and
    generating one or more control commands for adjusting settings of the one or more components based on the retrieved rules and personal setting data.

11. The system of claim 10, wherein the external condition includes one of a weather condition, a road condition, and a traffic condition in an area where is driving apparatus is traveling in.

12. The system of claim 10, wherein the condition information includes at least one of a fatigue condition and a medical condition regarding the user.

13. The system of claim 10, wherein the condition information include at least one of an ambient condition within a cabin of the driving apparatus, a mechanical condition of the driving apparatus, and an electrical condition of the driving apparatus.

14. The system of claim 10, wherein the personal setting data overrides the target setting specified in the given rule.

15. The system of claim 10, wherein the personal setting data specify at least one additional target setting for adjusting the component specified in the given rule.

16. The system of claim 10, wherein the component specified in the given rule includes at least one of: an audio module, air conditioning module, seat control module, interior lighting module, window control module, sunroof control module, mirror control module, and telecommunication module of the driving apparatus.

17. The system of claim 10, wherein the driving apparatus includes a vehicle, a train, a ship, or an airplane.

18. The system of claim 10, wherein the one or more processors are further caused by the machine-readable instructions to perform: receiving the personal setting data from the user via an interface, the interface being presented to user on a portable computing device associated with the user.

\* \* \* \* \*